United States Patent [19]

Shupack et al.

[11] 4,013,411

[45] Mar. 22, 1977

[54] METHOD FOR DETECTING HEPATITIS ASSOCIATED ANTIGEN

[75] Inventors: Saul I. Shupack, Wayne, Pa.; Stephen F. Malin, Burlington, Mass.

[73] Assignee: Villanova University, Villanova, Pa.

[22] Filed: July 19, 1974

[21] Appl. No.: 489,907

Related U.S. Application Data

[63] Continuation-in-part of Ser. No. 177,134, Sept. 1, 1971, abandoned.

[52] U.S. Cl. .............................. 23/230 B; 424/8; 424/12; 424/89; 424/287
[51] Int. Cl.$^2$ .................. G01N 31/02; G01N 33/16
[58] Field of Search .......... 424/8, 12, 287, 86, 424/89; 23/230 R, 230 B; 260/112 B; 252/408

[56] References Cited

OTHER PUBLICATIONS

Blumberg, Nat. Acad. Med., 44:112, 1566 (1968).
Alter, Blood, 27:3, 297 (1966).
Zuckerman, Nature, 223:569 (1969).
Anderson; J. Chem. Soc. (London) pt. 2, 1936 pp. 1042–1049.
Keller, Chem. Rev., vol. 28, 1941 pp. 229–234, 239–244.

Primary Examiner—Albert T. Meyers
Assistant Examiner—Anna P. Fagelson
Attorney, Agent, or Firm—Howson and Howson

[57] ABSTRACT

A method for testing biological materials, and especially those obtained from the human body, for the presence of the hepatitis associated antigen (HAA), in which Zeise's salt, or another water soluble platinum or palladium salt containing a trans directing group which enables the noble metal-containing moiety of the salt to react with the hepatitis associated antigen (HAA) or related materials, is mixed with the material to be tested in the presence of water, causing the formation of characteristic visible turbidity in the mixture which persists after agitation if HAA is present. Any slight turbidity observed initially in normal sera disappears upon agitation if the test sample is free from the hepatitis associated antigen. Also disclosed are test reagents consisting of the platinum and palladium salts in aqueous solutions containing non-interfering stabilizing salts such as sodium and potassium chloride and equivalents.

25 Claims, No Drawings

METHOD FOR DETECTING HEPATITIS ASSOCIATED ANTIGEN

CROSS REFERENCE

This application is a continuation-in-part of our copending application Ser. No. 177,134, filed Sept. 1, 1971 now abandoned.

BACKGROUND OF THE INVENTION

1. Field of the Invention

Beginning with the observation by B. S. Blumberg et al. in 1961 of a serological precipitin reaction between the blood serum of a multiply transfused patient and blood serum from an Australian aborigine, it has been established that an antigen exists which is commonly associated with hepatitis. See B. S. Blumberg et al. Nat. Acad. Med. 44:112, 1566, (1968) and H. S. Alter and B. S. Blumberg, Blood, 27:3, 297 (1966) and A. J. Zuckerman, Nature, 223:569 (1969). Originally known as the Australia antigen, this material is now generally referred to in the literature simply as the hepatitis associated antigen (HAA).

Hepatitis is clinically divided into two general categories, i.e., serum hepatitis, usually termed HBAg or type B hepatitis, and infectious hepatitis which is usually termed type A hepatitis. Serum hepatitis (type B) exists in at least two subtypes, i.e., a-d and a-y. The current available means of detection of hepatitis are primarily directed toward serum hepatitis (HBAg or type B) and are baed on the serological reaction of the antigen associated with the disease process. The antigen involved in this invention will be referred to hereinafter simply as HAA, but includes the high molecular weight protein associated with viral infection of the liver. This antigen (HAA) is extremely rare in the blood of the normal American population and has been reported to occur to an extent of less than 0.1%. The HAA antigen has been detected in patients suffering from acute myelogenous leukemia, chronic lymphocytic leukemia, and acute lymphocytic leukemia. The antigen (HAA) has also been detected in institutionalized patients with Down's syndrome who have a tendency to exhibit subacute hepatitis as reported by Krugman and others in the New England Journal of Medicine, 281:119-122, (1969). The HAA antigen, as indicated by its name, has been found to have a very high incidence in patients who have suffered infectious hepatitis. Inasmuch as a very large number of patients receiving transfusions of blood materials contract hepatitis due to the origin of the transfused blood materials, much work has been done in recent years and is still being done to reduce infection from this source. Much of this work has centered around schemes to detect the presence of the hepatitis associated antigen (HAA) in blood prior to administration of the blood or blood materials to the patient. Canadian Medical Association Journal, 106 Special Issue on Viral Hepatitis, February 26, 1972; *Austrailia Antigen and Hepatitis*, B. S. Blumberg, A. I. Sutnick, W. T. London and I. Millman, C.R.C. Press, Cleveland, Ohio, (1972).

2. The Prior Art

In general, the serological schemes previously proposed for the detection of HAA in blood depend upon the isoprecipitin reaction of antibody-containing serum, commonly found in multiply-transfused patients and currently produced in animals immunized with HAA, with the antigen (HAA) found most frequently in the serum of patients with hepatitis, or a lesser extent in the other disorders referred as above. Two well-known methods of this type are immunodiffusion (ID) and complement fixation (CF). Both of these methods require a minimum eight hour incubation period and are not, therefore, suitable as rapid screening techniques in blood banks. An electrophoretically enhanced diffusion; i.e., immunoelectroosmophoresis (IEOP) or counter-electrophoresis (CEP) has been recently developed by Prince and Burke (Scienes 169:593 (1970)). This method is very sensitive and can be carried out in about 30 minutes.

S. F. Malin and J. R. Edwards of Villanova University (Nature, New Biology 235 182 (1972)) have recently developed a latex inhibition assay (LAT) for HAA in which latex particles are employed as the indicator system. The agglutination of the particles indicates the presence of HAA. The assay is simple and rapid.

The American Association of Blood Banks has recommended that the presence or absence of HAA should be established as one of the criteria for the administration of blood and blood products prior to their administration. The currently accepted method for this purpose is RIA, but this stand has been strongly questioned in (Blood 43, 947, (1973)) and N. Eng. J. Med. 289, 385 (1973), due to its expense and the fact that blood shown to be negative by RIA has caused post-transfusion hepatitis. The radioimmuno assay (RIA), employs a radioactively labeled protein which combines with the HAA to give a radioactive antibody-antigen complex incorporating a radioisotope in an amount proportionate to the amount of HAA in the serum.

Inasmuch as whole blood and blood materials have a relatively short shelf life, there is a need for a rapid method for screening blood for the presence of HAA prior to administration. A truly rapid test would also have obvious utility in blood banks, since a potential donor's blood could be sampled and tested prior to withdrawing the main blood donation, thus saving the time and expense of collecting quantities of unusable blood.

A further disadvantage of previously proposed methods for testing for hepatitis is that HAA is the only hepatitis related antigen or protein which is indicated by the tests using hepatitis associated antibody. The specificity of the antibody-antigen reaction precludes reactions with dissimliar, but possibly related, antigens. Probably a major portion of the blood and blood products capable of transmitting hepatitis contain HAA as the causative agent or associated with the causative agent. However, it is possible that numerous other antigens or other high molecular weight proteins having a similarity to HAA may indicate and/or be capable of transmitting hepatitis. Such other antigens or proteins are not detected by previously known tests for hepatitis.

It is the primary object of the present invention therefore, to provide a rapid test for detecting the presence of HAA in biological materials and especially those obtained from the human body, particularly blood and blood materials.

It is another object of the invention to provide an improved test for detecting not only HAA, but also other agents in blood materials which cause or are associated with hepatitis, and which is simple enough to be carried out routinely by persons without specialized technical training.

SUMMARY OF THE INVENTION

The above and other objects of the present invention for detecting the presence of hepatitis or related diseases are attained by mixing a biological material, especially a material obtained from the human body, in the presence of water, with at least one water soluble platinum or palladium salt containing a trans directing group which enables the metal-containing moiety of the salt to react with HAA or related materials to form a detectable characteristic precipitate. More specifically, the following salts have been found to be operable for this purpose:

potassium ethylene platinum (II) trichloride (Zeise's salt),
potassium carbonyl platinum (II) trichloride,
cis, bis-triethylphosphine platinum (II) dichloride,
cis, bis-triphenylphosphine hydrido platinum (II) chloride
potassium trans-2-butene platinum (II) trichloride,
potassium cis-2-butene platinum (II) trichloride, and
potassium isobutene platinum (II) trichloride.

The invention also includes aqueous solutions of these salts stabilized with non-interfering salts, e.g., the alkali metal salts, among others.

The test is normally carried out at room temperature or, if desired, at a standard temperature such as 25° C. However, elevated temperatures as high as 37° C. are undesirable, since normal proteins tend to aggregate or flocculate with the test reagents at such temperatures and may give false positives.

It is not necessary that the cations in the foregoing salts be potassium, since sodium or any other suitable non-interfering cation could be employed as well, so long as the cation selected does not render the associated noble metal-containing moiety too insoluble in water to provide adequate concentrations for reaction with HAA. The cation must not, of course, be one known to cause the precipitation of serum proteins, since such a cation would interfere with the test. It is the reactive noble metal-containing moieties listed above and other equivalent platinum or palladium moieties containing trans directing groups which are the effective test reagents of the invention; the identity of the cation or other means for rendering the noble metal-containing moieties soluble being immaterial.

Platinum or palladium salts other than those specifically listed above which are sufficiently stable and soluble in water or which can be made sufficiently soluble, and which contains a trans directing group enabling the noble metal containing moiety to react with HAA or related materials to form the detectable characteristic precipitate can also be used in the invention. The valence state of the platinum and palladium moieties in the salts may vary. Also the trans directing group may be any such group which does not render the salt inoperable, and which has sufficient effect to render the noble metal-containing moiety sufficiently reactive with the HAA. The trans effect referred to is discussed in detail in Chapter 5, "Substitution Reactions of Square-Planar Complexes" in *Mechanisms of Inorganic Reactions A Study of Metal Complexes In Solution*, Second Edition, John Wiley & Sons, Inc., N.Y, (1967) by Fred Basolo and Ralph G. Tearson.

Inasmuch as Zeise's salt is the preferred reagent of the invention because of its availability, stability and excellent reactivity in the process, the invention will be discussed below primarily in conjunction with the use of this salt. It is to be understood, however, that the other specific salts listed above, and other platinum and palladium salts containing trans directing groups which enable them to react with HAA to form the detectable characteristic precipitate may also be used in the same way as Zeise's salt. Also, other square planar $d^8$ metal-containing complexes which contain ligands capable of exhibiting trans directing properties can be expected to interact in a similar manner. These other salts, of course, vary in availability, stability, solubility and reactivity for HAA and are, therefore, of varying degrees of desirability in the process of the invention.

When the Zeise'salt or any other salt operable in the invention is mixed with a sample containing HAA or other detectable material in the presence of water, a characteristic precipitate detectable as turbidity is formed in the resulting mixture. In normal serum a slight turbidity may appear but it disappears when agitated as by gentle shaking with the result that the initial turbidity clears. In samples containing HAA, on the other hand, the initial turbidity will not clear on gentle agitation as with normal blood material, but persists.

This simple and rapid test for the presence of HAA is based upon the surprising discovery that Zeise's salt appears to react specifically with HAA to form a precipitate which will not redissolve in aqueous liquid biological materials.

DETAILED DESCRIPTION OF THE INVENTION

Zeise's salt, which has been known since 1827, is now considered to have the formula $K[Pt(C_2H_4)Cl_3].H_2O$ in which the structure of the anion is

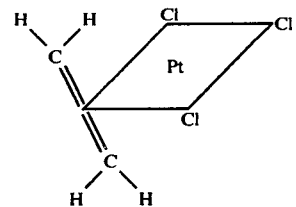

in which the ethylene moiety is oriented perpendicular to the $PtCl_3$ plane. See "A Redetermination of the Crystal and Molecular Structures of Zeise's Salt $K[Pt(C_2H_4)Cl_3].H_2O$" by J. A. J. Jarvis, B. T. Kilbourn and P. G. Owston in "Acta Crys", B27:366 (1971). The chlorine atom trans to the trans directing ethylene moiety is further removed from the platinum atom (2.42A) than the other chlorine atoms (2.32A), and, thus, is more easily reacted. Without prejudice or restriction to any theory of operation, it is presently believed that this trans effect permits reaction of the Zeise's salt with a sulfhydryl group in the antigen (HAA). It will be apparent to those skilled in the art that the chlorine atoms of the Zeise's salt could be replaced with iodine or bromine atoms; and that other olefins could replace the ethylene group, including both unsubstituted olefins and those substituted with non-interfering groups such as alkyl groups, among others, so long as the salts react with HAA to produce the characteristic detectable precipitate. Operable compounds of this reaction type would, therefore, be considered to be the equivalent of Zeise's salt for the purposes of the present invention.

Zeise's salt is soluble in water and physiological saline solution as well as other aqueous liquids. Therefore, the method of the invention may be carried out employing any liquid biological material such as serum, plasma, plasma fractions, or other aqueous solutions or suspensions of biological materials by the addition of solid Zeise's salt to such liquid materials. On the other hand, the method may be carried out employing solid blood materials and an aqueous solution of the Zeise's salt. While the necessary water may be supplied from either the biological material or Zeise's salt reagent as noted above, it is preferred to conduct the test employing both a liquid material and an aqueous solution of Zeise's salt.

The concentration of Zeise'salt in the reaction mixture containing water and biological material to be tested may vary widely and is not critical as long as sufficient Zeise's salt is present in solution to form a precipitate visible in the reaction mixture. In general, however, the Zeise's salt is conveniently employed in concentrations from about 0.1 to about 0.5% by weight based on the weight of the aqueous solutions; the preferred reagent being a 0.5% solution. Concentrations of less than 0.1% may be employed as long as a reliably detectable precipitate is obtained in the sample tested. Concentrations above 0.5% may also be employed, if desired, and indeed solid Zeise's salt itself may be used, as noted above, if the blood material is in a liquid form containing water. Concentrations above about 0.5% are not normally necessary to achieve a satisfactory test, however, and are, of course, uneconomic due to the high cost of Zeise's salt.

The test of the invention may be used to detect the presence of HAA in any type of biological material which is sufficiently clear in itself or which can be placed in solution or suspension in water or physiological saline so as to provide a test sample in which the Zeise's salt precipitate can be reliably detected. The test is, however, primarily intended to be employed on blood serum, plasma and blood products.

As is well-known, human blood normally contains about 40 to 50% solids in the form of blood cells and about 50 to 60% liquid or plasma or serum. While the term "serum" strictly speaking refers to the liquid portion of the blood after clotting or removal of the clotting factors and "plasma" generally refers to the total liquid portion of the blood after removal of the cells, the terms serum and plasma are used more or less interchangeably herein, since the distinction between the two is not critical in the present invention.

The cell content of blood is made up of formed elements, i.e., red cells (erythrocytes), white cells (leucocytes) and platelets. These cells may be separated from the plasma by known techniques such as by centrifugation and sedimentation. The plasma may be processed further by known techniques into various plasma fractions. Plasma and plasma fractions are available commercially in liquid, frozen and dried form. About 50% of the protein content of blood plasma is made up of albumin which is also available commercially. Gamma globulin can also be isolated along with other blood materials. All of the above materials, as well as others known to the art which may be derived from whole blood, may be tested for the presence of HAA according to the invention. Whole blood itself is not tested directly, however, since the presence of the red blood cells masks the Zeise's salt-HAA precipitate. Therefore, the simplest method of testing whole blood is to centrifuge a small sample and conduct the test of the invention on the clear plasma obtained in this way.

The specificity of Zeise's salt for HAA has been demonstrated by performing the test of the invention on a variety of "pure" proteins. The test was negative for the following materials: reconstituted human serum from which the antigen has been removed by gel filtration; serum alumbin; jaundiced human serum not containing HAA; and calf thymus deoxyribonucleic acid. The test was positive on the other hand for: an antigen (HAA) fraction isolated by gel filtration; HAA, immunoglobin M and gamma globulins precipitated from serum containing HAA; and commercially available HAA. It should be noted further that a test of the invention cannot be used on "freeze-dried" protein preparations since they react with Zeise's salt irrespective of the presence of HAA. Frozen or concentrated solutions can, however, be tested effectively.

It has also been demonstrated that platinum salts, other than Zeise's salt, and the other salts listed above as useful in the invention, even those known to be active against tumors, do not react with HAA. More specifically, no visible reaction was obtained between HAA and the following salts in serums provided positive by other methods.

| Compound | | |
|---|---|---|
| cis-Pt(IV) | $(NH_3)_2Cl_4$ | $K_2PtCl_4$ |
| cis-Pt(II) | $(NH_3)_2Cl_2$ | $K_2PdCl_4$ |
| Pt(II) | $(NH_2CH_2CH_2NH_2)Cl_2$ | $(C_6H_5CN)_2PdCl_2$ |
| Pt(IV) | $(NH_2CH_2CH_2NH_2)Cl_4$ | |

These salts, of course, are inoperable because they do not contain a trans directing group of sufficient strength in the noble metal-containing moiety.

It should also be noted that certain platinum and palladium salts have been found to give a positive reaction in sera known to be positive but which either give a slight positive reaction with sera known to be negative or decompose and precipitate free noble metal. In either case, the test result may be inconclusive, particularly with respect to negative sera and especially in other than expert hands, and thus, it is not generally desirable to employ such salts in the invention since Zeise's salt and others are available which provide non-ambiguous results.

Since some preservatives used in serum samples may interfere with the test of the invention, one must avoid such materials, e.g., sodium azide and merthiolate should not be present. Sodium fluoride in "normal" does not interfere with the test however. Aqueous solutions of the test reagents or the materials being tested may, however, contain any salt or other material in any concentration which does not interfere with the test. More specifically, it has been found that the shelf life of aqueous solutions of the test reagents listed above may be extended by the incorporation of alkali metal salts in any suitable concentration. While any soluble alkali metal salt which does not contain an interfering anion may be employed, it has been found that sodium and potassium chloride are both effective to stabilize aqueous solutions of Zeise's salt and the other test reagents listed above, and are, therefore, generally preferred for this purpose due to their low cost and ready availability. Cesium chloride, which is present in a concentration of 1.29g/ml in some commercially available HAA preparations, does not interfere with the test.

While the preferred stabilizing agent for aqueous solutions of Zeise's salt of the other test reagents is physiological saline, i.e., about 0.9% aqueous sodium chloride, the alkali metal or other salts may be employed over a wide range of concentrations from at little as 0.01% to as much as 1 molar solutions or higher.

It will be understood, of course, that the test of the present invention may be performed on specimens and samples other than blood serum or blood plasma per se, although this is anticipated to be the primary use. Thus, the test may be used as an indicator for antigens and other agents related to hepatitis which have been isolated or recovered from physiologic materials (e.g., from stools or ascites fluid). It will be understood that where the test is used on samples other than blood serum or plasma, the relative amounts of reagent to be added to the sample may differ depending on the particular concentration or dilution of the specimen to be tested.

After addition of the reagent, the biological sample and reagent are gently mixed, preferably after standing about fifteen seconds. The mixture is then allowed to stand at room temperature for 5 minutes. The sample, such as blood serum, is normally clear, and a precipitate or slight turbidity will immediately form whether the test is ultimately negative or positive. If the test is negative, this initial precipitate or turbidity will disappear upon mixing, but will persist upon mixing in the case of an HAA-containing sample.

Any turbidity or precipitate remaining after mixing and standing for 5 minutes is considered a positive test. The test sample with reagent added is preferably compared to a known negative and a known positive, although a negative should be perfectly clear. It is best to compare the test serum or other sample with one that has been treated with an equal volume of physiological saline. The difference in absorbance of light at a wavelength of approximately 600 nm between a specimen treated with saline and an identical specimen treated with Zeise's salt can be used as a quantitative measure of the extent of the reaction. It is believed that an absorbance difference of 0.05–0.10 between the specimen treated with saline and that treated with Zeise's salt indicates a positive reaction. An absorbance difference of less than 0.010 is considered negative for HAA. Usually, a positive test will become more pronounced after standing. Although a positive test usually appears only turbid or cloudy, a whitish precipitate may be observed in the case of a heavy positive reaction. The reaction is greatly enhanced by allowing the mixture to incubate at 4° C. for 24 hours.

Although we do not wish to be bound by any particular theory, it is believed that the reagent of the present invention reacts with, and thereby detects the presence of, high molecular weight proteins which are found in the blood of persons infected with or carrying (i.e., capable of transmitting) hepatitis. Such high molecular weight proteins include, but are not limited to the hepatitis associated antigen. Hence, an advantage of the test of the present invention over previously known tests is believed to be the ability to detect not only HAA, but also high molecular weight protein agents, which may or may not be antigens, although similar to HAA and which also indicate the presence of hepatitis infection or contaminants in the blood. Another advantage of the test of the present invention is the rapidity with which it may be performed. Hence, this test could suitably be used to screen blood samples initially, being followed by one of the previously known tests as a back-up.

Hepatitis is a disease which affects only human beings and other primates and is quite different from similar diseases affecting other species. Consequently, tests of human blood samples made by injection into other animals do not produce meaningful results. Furthermore, due to the severity of hepatitis, the testing of blood samples by injection into other humans in generally not feasible. Moreover, due to the prevailing uncertainty in the present state of the art as to the exact agents which cause or carry hepatitis disease, it is impossible to determine with certainty whether or not a given sample of blood serum is capable of transmitting certain forms of the disease.

Consequently, there is no absolute standard, short of injection of blood serum into humans, against which tests for hepatitis may be evaluated. Therefore, the effectiveness of new tests must be evaluated by comparison with the results obtained by previously existing tests for the disease. Accordingly, the relative accuracy of the test of the present invention will now be demonstrated with reference to the following comparative test panels.

EXAMPLE I

In order to demonstrate the effectiveness of the method of the invention, 124 different sera were tested by this method as well as the latex agglutination test (LAT), immunodiffusion (ID) and complement fixation (CF) tests. The tests of the present invention were performed using 5 drops of 0.3% aqueous Zeise's salt in 0.4 ml samples of sera. The LAT tests were conducted as described in Malin and Edwards (Nature, 235 182 (1972)). The immunodiffusion (ID) tests were performed in the usual manner using 1% agar and allowing the diffusion to proceed on the plate for 24 hours at 25° C. (See B. S. Blumberg et al. Lancel II, 634 (1961). The complement fixation (CF) assays were performed in the usual manner using 25 ml quantities of the various components. (See R. H. Purcell et al. J. Inf. Dis., 120:3, 383, 1969 and N. R. Shulman et al. Science, 165:304 (1969).

Each of the 124 sera was tested by each of the four methods (Zeise's salt; LAT; ID; and CF) and the result, positive or negative for the presence of HAA tabulated in Table I below. Table I also shows the number of percentage of the total number of sera having each of 10 different overall combinations of response to the four tests.

TABLE I

Statistical Analysis of the Results of Serological and Zeise's Salt Tests For The Hepatitis Associated Antigen In Samples of Blood Plasma

| TEST | | | Zeise's | No. of | % of Total |
|---|---|---|---|---|---|
| LAT | ID | CF | Salt | Samples | Samples |
| + | + | + | + | 30 | 24.2 |
| + | − | − | + | 1 | 0.8 |
| − | + | + | + | 6 | 4.8 |
| + | − | + | + | 2 | 1.7 |
| − | − | − | + | 9 | 7.3 |
| − | − | − | − | 67 | 54.0 |
| + | − | − | − | 1 | 0.8 |
| + | − | + | − | 3 | 2.4 |
| + | + | + | − | 4 | 3.2 |
| + | − | − | − | 1 | 0.8 |
| Total | | | | 124 | 100.0 |

Referring to Table I, the four tests produced the overall positive-negative response percentages shown in Table II.

TABLE II

|  | LAT | ID | CF | Zeise's Salt |
|---|---|---|---|---|
| % Positive | 33.9 | 33.9 | 31.5 | 38.8 |
| % Negative | 66.1 | 66.1 | 68.5 | 61.2 |

Analyzing the above data further, and taking any positive result for any of the four tests as positive, but requiring all four tests to be negative for a negative, the overall agreement of the tests was shown in Table III below.

TABLE III

| Agreement: | % | | % |
|---|---|---|---|
| Positive | 46.0 | False Positive | 7.3 |
| Negative | 54.0 | False Negative | 7.3 |

The percentages of false positive and false negative results for each of the four tests are shown in Table IV below.

TABLE IV

|  | LAT | ID | CF | Zeise's Salt |
|---|---|---|---|---|
| % False Positive | 2.8 | 6.6 | 6.0 | 7.3 |
| % False Negative | 6.2 | 3.3 | 6.3 | 7.3 |

While the false positive and false negative responses for the test of the invention are somewhat higher than for the tests of the prior art, the new method has the distinct advantage over the other tests of being capable of being carried out in a few minutes even by unskilled personnel, whereas the LAT test requires an incubation period of 15 minutes, the ID, CF and RIA tests require incubation periods of 8 to 24 hours. The currently accepted methods do not detect HAA in all samples since post-transfusion hepatitis has not been eliminated.

EXAMPLE II

A total of 722 samples of blood serum was tested with both the test method of the present invention and the immunoelectroosmophoresis (IEOP or CEP) method described in the literature referred to above. The random samples tested were obtained for commercial blood banks, U. S. Army Hospitals and local hospitals in the Philadelphia, Pa. area. The reagent of the present invention which was used comprised 0.3% Zeise's salt dissolved in deionized water. Three drops of the test reagent were added to 0.2 ml of each specimen in a test tube. The test samples containing reagent were mixed after fifteen seconds and then allowed to stand at room temperature for sixty seconds before the result was observed. A statistical summary of the results of these two tests on the 722 samples tested is presented in Table V. The summary shows excellent agreement between the tests of the present invention and the standard commercially licensed IEOP (or CEP) test. The false negative and false positive statistics in this table are calculated on the assumption that the standard IEOP test is 100% accurate, which assumption is highly idealistic and made only for the purpose of comparison of the two methods.

TABLE V

| Total Samples Tested | 722 | 100% |
|---|---|---|
| Total Agreement | 623 | 86.5% |
| IEOP Positive - Zeise's Negative (i.e., Zeise's false negative) | 39 | 5.4% |
| IEOP Negative - Zeise's Positive (i.e., Zeise's False Positive) | 60 | 8.3% |
| Total IEOP Positive | 124 | 17.2% |
| Total IEOP Negative | 598 | 82.8% |
| Total Zeise's Positive | 144 | 19.8% |
| Total Zeise's Negative | 578 | 80.2% |

EXAMPLE III

Another test panel was devised using serums from selected sources which had been serologically assayed by IEOP and RIA. The Zeise's salt concentration was 0.5% and all serums were compared against the serum diluted with saline.

TABLE VI

| Total samples tested | 71 | 100% |
|---|---|---|
| Serological positive and Zeise's salt negative | 1 | 1.4% |
| Serological negative and Zeise's salt positive | 20 | 29% |
| Total serological positive | 40 | 56.3% |
| Total serological negative | 31 | 43.7% |
| Total Zeise's salt positive | 60 | 84.5% |
| Total Zeise's salt negative | 11 | 14.5% |
| Total Agreement | 50 | 71.5% |

The larger number of sera indicated to be positive by Zeise's salt is in accord with the number of cases of post-transfusion hepatitis known to occur from blood which was declared negative for HAA by IEOP or RIA (See Blood, 42 947, (1973) and N. Engl. J. Med. 289, 385 (1973).

EXAMPLE IV

A third panel (Table VII) was employed using the U. S. Department of Biological Standards test panel number 2 for type B hepatitis associated antigen. The panel has been tested in many laboratories and by ID, CF, IEOP and RIA. In order to provide an objective basis for comparison, the turbidity of the precipitate obtained in the positive tests was assayed as follows employing a spectrophotometer. A wavelength of 600 nm was selected for the light employed since Zeise's salt does not absorb at that wavelength and thus any unreacted reagent could not interfere with the determination. A microcell was employed which permitted reading absorbancies of samples as small as 0.1 ml. The samples consisted of 200 $\mu$l of sera and 200 $\mu$l of a 5mg/ml solution of Zeise's salt mixed together in a test tube. A blank consisting of 200 $\mu$l of sera and 200 $\mu$l of 0.85% sodium chloride was also set up. The spectrophotometer was set for 100% transmission using the saline blank and the differential absorbance of each test sample was determined and recorded in Table VII below after mixing and standing for 5 minutes at room temperature.

TABLE VII

U.S. DEPARTMENT OF BIOLOGICAL STANDARDS TEST PANEL NUMBER 2 FOR HEPATITIS ASSOCIATED ANTIGEN

| Serum Number | DBS Reaction | Zeise's Salt Reactivity | | | |
|---|---|---|---|---|---|
| | | Visual 5 Min. | Turb. 5 Min. | Visual 4° C/18h | Turb. 4° C/18h |
| 201 | B | P | 0.35 | P | 0.670 |
| 202 | B | P | 1.50 | P | Infinity |
| 203 | N | P | 0.180 | P | 0.400 |
| 204 * | C | P | 0.305 | | |
| 205 | A | P | 0.275 | P | 0.600 |
| 206 | (B) | P | 0.780 | P | 1.50 |
| 207 | N | (P) | 0.140 | P | 0.255 |
| 208 | A | P | 0.580 | P | 1.20 |
| 209 | A | P | 0.180 | P | 0.400 |
| 210 | A | P | 0.200 | P | 0.540 |
| 211 | N | P | 0.270 | P | 0.510 |
| 212 | N | P | 0.470 | P | 1.000 |
| 213 | A | P | Infinity | P | Infinity |
| 214 | A | P | 0.230 | P | 0.480 |
| 215 | N | P | 1.40 | P | 1.70 |
| 216 | N | N | 0.090 | P | 0.490 |
| 217 | A | P | 0.620 | P | 1.100 |
| 218 | A | P | 0.280 | P | 0.800 |
| 219 | B | P | 0.680 | P | 0.900 |
| 220 | B | P | 0.420 | P | 0.810 |
| 221 | N | N | 0.090 | P | 0.310 |
| 222 | (A) | P | 0.580 | P | 0.950 |
| 223 | A | P | 0.390 | P | 0.610 |
| 224 | N | P | 0.180 | P | 0.270 |
| 225 | N | P | 0.210 | P | 0.350 |
| 226 | (A) | P | 0.320 | P | 0.450 |
| 227 | N | N | 0.100 | P | 0.170 |
| 228 | A | P | 1.500 | P | 1.900 |
| 229 | N | P | 0.220 | P | 0.460 |
| 230 | N | P | 0.200 | P | 0.330 |
| 231 | N | N | 0.080 | P | 0.340 |
| 232 | A | P | 0.850 | P | 1.250 |
| 233 | N | P | 0.210 | P | 0.610 |
| 234 | A | P | 0.400 | P | 0.590 |
| 235 | A | P | Infinity | P | Infinity |
| 236 * | (C) | P | 0.070 | | |
| 237 * | (C) | (P) | 0.040 | | |
| 238 | B | P | 0.240 | P | 0.340 |
| 239 | B | P | 0.840 | P | 1.200 |
| 240 | N | N | 0.020 | N | 0.100 |
| 241 | N | (P) | 0.110 | P | 0.200 |
| 242 | N | P | 0.400 | P | 0.850 |
| 243 * | C | P | 0.312 | | |
| 244 | B | P | 0.390 | P | 0.570 |
| 245 * | (C) | P | 0.288 | | |
| 246 * | (C) | P | 0.405 | | |
| 247 | N | (P) | 0.160 | P | 0.310 |
| 248 | N | P | 0.240 | P | 0.260 |
| 249 * | C | P | 0.400 | | |
| 250 | (B) | P | 0.300 | P | 0.700 |
| 251 | A | P | 0.250 | P | 0.390 |
| 252 | A | P | 2.000 | P | Infinity |
| 253 | A | P | 0.205 | P | 0.340 |
| 254 | A | P | 0.900 | P | 1.250 |
| 255 | A | P | 1.200 | P | 1.500 |
| 256 | A | P | 1.800 | P | Infinity |
| 257 * | (C) | P | 0.130 | | |
| 258 | N | P | 0.185 | P | 0.320 |
| 259 * | (C) | P | 0.850 | | |
| 260 | A | P | Infinity | P | Infinity |
| 261 * | C | P | 0.348 | | |

CODE OF REACTIVITY
A Reactive by all methods including immunodiffusion (ID)
B Reactive by immunoelectroosmophoresis (IEOP)
C Reactive by more sensitive assays including radioimmunoassay (RIA)
P Positive
N Negative
( ) Indicates borderline reactivity for the level of detection. Borderline sera for A are expected positive at level B and borderline sera for B are expected positive at level C.
* See Table VIII In this series of tests, 14 more samples were found positive by Zeise's salt than by other test methods including RIA. The order of magnitude of these additional positives is in accord with actual experience in post-transfusion hepatitis with RIA tested blood. There were no sera found negative by Zeise's salt that were found positive by other means. Selected sera were diluted, retested and still found positive by the Zeise's salt reaction. The sera were selected on the basis of being positive by RIA, the most sensitive assay previously known, and negative by IEOP, the next most sensitive assay of the prior art (Table VIII).

TABLE VIII

Dilutions of selected samples from the DBS test panel number of 2 for HAA. Seras were selected that were reactive only by RIA (category C).

| Sample Number | Dilution | A₆₀₀ | Reactivity |
|---|---|---|---|
| 204 | 0 | .305 | P |
|  | 1:2 | 0 | N |
| 236 | 0 | .070 | P |
|  | 1:2 | 0 | N |
| 237 | 0 | .040 | (P) |
|  | 1:2 | 0 | N |
| 243 | 0 | .312 | P |
|  | 1:2 | .022 | (P) |
|  | 1:4 | 0 | N |
| 245 | 0 | .288 | P |
|  | 1:2 | .078 | P |
|  | 1:4 | 0 | N |
| 246 | 0 | .405 | P |
|  | 1:2 | .145 | P |
|  | 1:4 | 0 | N |
| 249 | 0 | .400 | P |
|  | 1:2 | 0.050 | (P) |
|  | 1:4 | 0 | N |
| 257 | 0 | .130 | P |
|  | 1:2 | 0 | N |
| 259 | 0 | .850 | P |
|  | 1:2 | .270 | P |
|  | 1:4 | .075 | P |
|  | 1:8 | 0 | N |
| 261 | 0 | .348 | P |
|  | 1:2 | .060 | P |
|  | 1:4 | 0 | N |

P Positive
N Negative
( ) Borderline reactivity

Most of the sera could be diluted at least 1:2. The criteria for a positive sera was a difference in light absorbance, measured at a wavelength of 600 nm, of at least 0.05 units compared to the saline diluted sera.

EXAMPLE V

Several other types of biological fluids were tested for HAA using 0.5% aqueous Zeise's salt. The assay was performed in the usual fashion (addition of Zeise's salt solution and agitation).

TABLE IX

Selected reactions of HAA-containing fluids with Zeise's salt:
1. HAA serum diluted 1:125; IEOP positive and RIA positive. Zeise's salt positive.
2. HAA serum diluted 1:125; IEOP negative and RIA positive. Zeise's salt positive.
3. Stool suspension (purified and suspended in brain-heart infusion plus 0.5% bovine albumin) containing type A hepatitis "antigen"; type B negative measured by RIA. Zeise's salt positive.
4. Human ascites fluid containing type B hepatitis, subtype a-y. Zeise's salt positive.
5. A-2 placque virus (known to stimulate HAA antigenicity). Zeise's salt negative.
6. Rabbit globulin that agglutinates red blood cells coated with HAA (types a-d and a-y). Zeise's salt positive.

The foregoing results indicate that fluids, other than blood, containing HAA react with Zeise's salt.

As noted above, the Zeise's salt test of the present invention may be used to quickly detect HAA in any biological material that is clear enough in itself to permit perception of the persistent HAA Zeise's salt precipitate or which can be dissolved or suspended in water or saline solution to yield a mixture of sufficient clarity to permit observation of the test result. Therefore, virtually any blood material except whole blood itself can be tested directly. Whole blood can, of course, be quickly tested by simply separating the cells from the serum or plasma by the use of a centrifuge and the test carried out on the resulting clear liquid. Inasmuch as the test merely requires mixing a sample of blood material and a small quantity of the reagent, either Zeise's salt or preferably a dilute aqueous solution of Zeise's salt with the blood material in a test tube, shaking the tube gently, and then observing whether or not the resulting precipitate dissolves, it can be carried out by any designated person without medical, nursing, clinical or other special training. The test is, therefore, useful in blood banks either for testing samples of blood serum before taking the full blood donation from the donor, or to screen out HAA contaminated donations from a large number of such donations prior to further processing or use. The test is, of course, uniquely useful in hospital or other emergency rooms to quickly test the blood of a donor prior to an emergency transfusion, since no other test is available which can detect the presence of HAA in a blood sample in a matter of seconds. It is also possible to adapt this method to an automated system where the specimen is mixed with Ziese's salt, agitated, and the absorbance (turbidity) measured in a colorimeter, spectrophotometer or nephelometer.

The presently preferred practice is that of Example IV above, i.e., to employ 200 l samples of the sera to be tested and 200 μl additions of 0.5% aqueous Zeise's salt (5 mg/ml). The results of the tests are then read visually or, if desired, the turbidity of positive tests may be determined as in Example IV above.

Test reagents for use in the present invention are prepared by simply dissolving one of the reagent salts in water to the desired concentration, e.g., 5 mg of Zeise's salt per ml of water makes the preferred 0.5% aqueous solution. The shelf life of such a solution may be markedly extended as indicated above by also dissolving a non-interfering salt of an alkai metal in the reagent solution to a concentration of from about 0.01% up to one molar or even higher concentrations. The preferred agent solutions are stabilized are stabilized with sodium or potassium chloride since these salts are highly effective and readily available. As previously noted, virtually any concentration, of such a salt aids in stabilizing the reagent solutions, but in general about 1% or somewhat less is sufficient. Therefore, it is convenient to use physiological saline which contains about 0.85 to 0.9% sodium chloride or the equivalent, in making up the reagent solutions; the selected reagent salt being simply dissolved in the standard saline solution to the desired concentration.

What is climed is:
1. A method for testing biological materials for the presence of the hepatitis associated antigen which comprises contacting a biological material to be tested, in the presence of water, with at least one water soluble reagent selected from the group consisting of
   cis, bis-triethylphosphine platinum (II) dichloride,
   cis, bis-triphenylphosphine hydrido platinum (II) chloride,
and the anions
   ethylene platinum (II) trichloride,
   carbonyl platinum (II) trichloride,
   trans-2-butene platinum (II) trichloride, and
   isobutene platinum (II) trichloride,
said anions being associated with a non-interfering cation; said contact producing a characteristic presistent precipitate detectable in the reaction mixture if the biological material contains the hepatitis associated antigen, whereas any precipitate formed initially is not persistent if the biological material is free of said antigen.

2. The method of claim 1 in which the biological material is a solid dissolved or suspended in water to form test sample having a clear aqueous phase in which the characteristic precipitate can be reliably detected.

3. The method of claim 2 in which the biological material is a stool sample.

4. The method of claim 2 in which the biological material is blood platelets.

5. The method of claim 2 in which the biological material is albumin.

6. The method of claim 2 in which the biological material is a frozen blood material.

7. The method of claim 2 in which the biological material is a blood clotting factor.

8. The method of claim 1 in which an aqueous solution of at least one of said reagents is mixed with the material to be tested.

9. The method of claim 8 wherein the aqueous reagent solution is stabilized with at least one non-interfering alkali metal salt.

10. The method of claim 9 wherein the aqueous reagent solution consists essentially of the reagent in solution in physiological saline solution.

11. The method of claim 10 wherein the reagent is potassium ethylene platinum (II) trichloride.

12. The method of claim 9 wherein the reagent is potassium ethylene platinum (II) trichloride and the biological material is ascites fluid.

13. The method of claim 1 wherein the biological material is a human blood material.

14. The method of claim 13 wherein the blood material is in liquid form and contains water and the reagent is potassium ethylene platinum (II) trichloride in solid form.

15. The method of claim 13 wherein the blood material is blood serum.

16. The method of claim 13 wherein the blood material is plasma.

17. The method of claim 13 wherein the blood material is gamma globulin.

18. The method of claim 13 wherein the blood material is in liquid form and the reagent is potassium ethylene platinum (II) trichloride in aqueous solution.

19. The method of claim 18 wherein the blood material is serum.

20. The method of claim 18 wherein the blood material is plasma.

21. The method of claim 18 wherein the blood material is gamma globulin.

22. The method of claim 8 wherein the aqueous solution contains from about 0.1 to about 0.5% potassium ethylene platinum (II) trichloride by weight.

23. The method of claim 8 wherein 200 $\mu$l of a 0.5% solution of potassium ethylene platinum (II) trichloride are added to a 200 $\mu$l sample of the material to be tested.

24. The method of claim 22 wherein the solution is stabilized with sodium chloride.

25. The method of claim 22 wherein the solution is stabilized with potassium chloride.

* * * * *